(12) United States Patent
Lo et al.

(10) Patent No.: US 8,748,100 B2
(45) Date of Patent: Jun. 10, 2014

(54) METHODS AND KITS FOR SELECTIVELY AMPLIFYING, DETECTING OR QUANTIFYING TARGET DNA WITH SPECIFIC END SEQUENCES

(75) Inventors: Yuk Ming Dennis Lo, Hong Kong (CN); Yu Kwan Tong, Hong Kong (CN); Wai Kwun Rossa Chiu, Hong Kong (CN); Chunming Ding, Hong Kong (CN)

(73) Assignee: The Chinese University of Hong Kong, Hong Kong (CN)

( * ) Notice: Subject to any disclaimer, the term of this patent is extended or adjusted under 35 U.S.C. 154(b) by 1262 days.

(21) Appl. No.: 11/897,654

(22) Filed: Aug. 30, 2007

(65) Prior Publication Data

US 2009/0061425 A1    Mar. 5, 2009

(51) Int. Cl.
C12Q 1/68 (2006.01)
C07H 21/04 (2006.01)
C12N 9/16 (2006.01)

(52) U.S. Cl.
USPC ....... 435/6.12; 536/24.3; 536/24.33; 435/196

(58) Field of Classification Search
None
See application file for complete search history.

(56) References Cited

U.S. PATENT DOCUMENTS 7,901,884 B2 * 3/2011 Lo et al. .................. 435/6.11
2005/0266418 A1 * 12/2005 Chen et al. ............... 435/6
2009/0203002 A1 * 8/2009 Brown .................... 435/6

OTHER PUBLICATIONS

Chim et al. Detection of the placental epigenetic signature of the maspin gene in maternal plasma. PNAS 102(41):14753-8, Oct. 11, 2005.*
Zhang et al. Transactivation through Ets and Ap1 transcription sites determines the expression of the tumor-suppressing gene maspin. Cell Growth & Differentiation 8:179-186, Feb. 1997.*
Yamada et al. A comprehensive analysis of allelic methylation status of CpG islands on human chromosome 21q. Genome Res 14:246-266 (2004).*
Chim, Stephen S.C. et al., "Detection of the Placental Epigenetic Signature of the *Maspin*Gene in Maternal Plasma," *PNAS*41(102): 14753-14758, Oct. 11, 2005.
Tong, Yu K. et al., "Noninvasive Prenatal Detection of Fetal Trisomy 18 by Epigenetic Allelic Ratio Analysis in Maternal Plasma: Theoretical and Empirical Considerations," *Clinical Chemistry*52(12): 2194-2202, 2006.

* cited by examiner

*Primary Examiner* — Samuel Woolwine
(74) *Attorney, Agent, or Firm* — Seed IP Law Group, PLLC (57) ABSTRACT

Disclosed herein are methods and kits for selectively amplifying, detecting or quantifying a DNA fragment with a specific end sequence, especially generated following restriction enzyme digestion. This method can be used, for example, to detect a hypomethylated DNA fragment. This methods and kits are especially useful in detecting or quantifying a hypomethylated fetal DNA fragment in a maternal plasma sample containing a corresponding hypermethylated maternal DNA fragment.

43 Claims, 3 Drawing Sheets

Fig. 3

METHODS AND KITS FOR SELECTIVELY AMPLIFYING, DETECTING OR QUANTIFYING TARGET DNA WITH SPECIFIC END SEQUENCES

BACKGROUND

1. Technical Field

The present invention generally relates to methods and kits for selectively amplifying, detecting or quantifying a DNA fragment with a specific end sequence, especially that created by a restriction enzyme, in a sample containing other DNA fragments.

2. Description of the Related Art

The discovery of cell-free fetal nucleic acids in the plasma of pregnant women has opened up new possibilities for non-invasive prenatal diagnosis and monitoring (Lo et al., *Lancet*, 350:485-7 (1997); Lo and Chiu, *Nat Rev Genet*, 8:71-77 (2007)). Over the past decade, a list of described fetal-specific markers have expanded from gender-dependent Y-chromosomal sequences (Lo et al., *Am J Hum Genet*, 62:768-75 (1998); Lo et al., *Clin Chem*, 45:1747-51 (1999); Leung et al., *Lancet*, 352:1904-5 (1998); and Rijnders et al., *Prenat Diagn*, 23:10424 (2003)) and paternally-inherited polymorphic markers (Lo et al., *N Engl J Med*, 339:1734-8 (1998); Saito et al., Lancet, 356:1170 (2000); Chiu et al., *Lancet*, 360:998-1000 (2002); and Chow et al., *Clin Chem*, 53:141-2 (2007)) to universal fetal markers such as placental-specific mRNA transcripts (Ng et al., *Proc Natl Acad Sci USA*, 100:4748-53 (2003); Tsui et al., *J Med Genet*, 41:461-7 (2004); and Lo et al., *Nat Med*, 13:218-223 (2007)) and those dependent on placental-specific epigenetic signatures (Chim et al., *Proc Natl Acad Sci USA*, 102:14753-8 (2005); Tong et al., *Clin Chem*, 52:2194-202 (2006); and Chan et al., *Clin Chem*, 52:2211-8 (2006)). In addition to clinical applications, such as prenatal gender determination and prenatal RHD genotyping, researchers have recently demonstrated that trisomy 21 and trisomy 18 pregnancies could be inferred by the analysis of fetal nucleic acids in maternal plasma samples (Lo and Chiu, *Nat Rev Genet*, 8:71-77 (2007)).

The tumor suppressor gene SERPINB5 (maspin), which is expressed in placenta (Dokras et al., *Placenta*, 23:274-80 (2002)) and exhibits a tissue-specific methylation pattern (Futscher et al., *Nat Genet*, 31:175-9 (2002)), is the first universal fetal epigenetic marker reported (Chim et al., *Proc Natl Acad Sci USA*, 102:14753-8 (2005)). To detect hypomethylated placental SERPINB5 in an excess background of hypermethylated SERPINB5 of maternal origin in a maternal plasma sample, the use of bisulfite treatment was reported (Frommer et al., *Proc Natl Acad Sci USA*, 89:1827-31 (1992); and Herman et al., *Proc Natl Acad Sci USA*, 93:9821-6 (1996)). However, it was documented that up to 96% of the DNA in the plasma sample would be degraded by the bisulfite treatment (Grunau et al., *Nucleic Acids Res*, 29:E65-5 (2001)), leaving a minute amount of DNA for analysis. In a recent study, Chan et al. have described the discovery and possible utility of another universal fetal marker in maternal plasma (Chan et al., *Clin Chem*, 52:2211-8 (2006)). This marker, the RASSF1A tumor suppressor gene, exhibits an opposite methylation pattern in the placenta and maternal blood cells to the SERPINB5 gene (Chiu et al., *Am J Pathol*, 170:941-50 (2007)). In this case, methylation analysis involving the use of methylation-sensitive restriction endonucleases could be employed, thus cutting the hypomethylated RASSF1A from maternal blood cells and leaving the hypermethylated placental RASSF1A intact for amplification.

If the same approach were to be applied to the detection of the placenta-derived hypomethylated SERPINB5 molecules, an endonuclease which exhibits an opposite action to the methylation-sensitive restriction endonucleases described above would be needed. In the current literature, it has been reported that the McrBC enzyme, which is an endonuclease, would cleave methylcytosine-containing DNA sequences (Sutherland et al., *J Mol Biol*, 225:327-48 (1992)). However, not much is known about the exact molecular action of this enzyme, and the cleavage spacing can range from 32 basepairs to two kilobases long (Stewart et al., *Biol Chem*, 379: 611-6 (1998)). For experiments which require high precision, as in the case of detecting fetal DNA in maternal plasma, such an enzyme would not be reliable.

A potential approach would be to develop a specific method for the detection of the restriction products of hypomethylated SERPINB5 sequences following a methylation-sensitive restriction endonuclease treatment. To allow this to be done, a new method which can specifically detect a shorter DNA fragment (i.e. restricted) in the presence of an excess of longer DNA fragments (i.e. unrestricted) is needed.

BRIEF SUMMARY

According to a first aspect of the present invention, there is provided a method for selectively amplifying a target DNA fragment with a specific end sequence in a sample containing other DNA fragments. According to one embodiment of the method, it comprises:

(a) contacting the sample with a stem-loop primer, wherein the 3' portion of the stem-loop primer is complementary to the 3' end of a strand of the target DNA fragment on the specific end sequence, while the 5' portion of the stem-loop primer is capable of forming a stem-loop structure;

(b) annealing the stem-loop primer to the strand of the target DNA fragment via the 3' portion thereof and performing an extension reaction by using the strand of the target DNA fragment as a template; and (c) amplifying the extension product to obtain an amplified product of the target DNA fragment.

According to a second aspect of the present invention, there is provided a method for selectively amplifying a hypomethylated target DNA fragment which has been cut by a methylation-sensitive restriction enzyme in a sample containing a corresponding hypermethylated DNA fragment which is not cut by the same enzyme. One embodiment of the method comprises:

(a) contacting the sample with a stem-loop primer, wherein the 3' portion of the stem-loop primer is complementary to the 3' end of a strand of the hypomethylated target DNA fragment at the cut site, and the 5' portion of the stem-loop primer is capable of forming a stem-loop structure;

(b) annealing the stem-loop primer to the strand of the hypomethylated target DNA fragment via the 3' portion thereof and performing an extension reaction by using the strand of the hypomethylated target DNA fragment as a template; and (c) amplifying the extension product to obtain an amplified product of the hypomethylated target DNA fragment.

According to a third aspect of the present invention, there is provided a method for detecting and/or quantifying a hypomethylated target DNA fragment in a sample containing a corresponding hypermethylated target DNA fragment, wherein both the hypomethylated target DNA fragment and the corresponding hypermethylated target DNA fragment contain a methylation-sensitive restriction enzyme recognition site. Due to the methylation-sensitive nature of the enzyme, the hypomethylated target will be cut but the hypermethylated target will not be cut. One embodiment of the method comprises:

(a) digesting the sample with a methylation-sensitive restriction enzyme which recognizes the methylation-sensitive restriction enzyme recognition site;

(b) contacting the digested sample with a stem-loop primer, wherein the 3' portion of the stem-loop primer is complementary to the 3' end of a strand of a digested target DNA fragment at the methylation-sensitive restriction enzyme recognition site, while the 5' portion of the stem-loop primer is capable of forming a stem-loop structure;

(c) annealing the stem-loop primer to the strand of the digested target DNA fragment via the 3' portion thereof and performing an extension reaction by using the strand of the digested target DNA fragment as a template; and (d) detecting and/or quantifying the extension product with a PCR assay, wherein one primer of the primer pair used in the PCR assay is specific to the stem-loop primer, wherein results of the PCR assay indicate the presence and/or quantity of the hypomethylated target DNA fragment in the sample.

According to a fourth aspect of the present invention, there is provided a method for detecting and/or quantifying a hypomethylated fetal DNA fragment in a maternal plasma sample containing a corresponding hypermethylated maternal DNA fragment, wherein both the hypomethylated fetal DNA fragment and the corresponding hypermethylated maternal DNA fragment contain a methylation-sensitive restriction enzyme recognition site. Due to the methylation-sensitive nature of the enzyme, the hypomethylated fetal DNA target will be cut but the hypermethylated maternal DNA target will not be cut. One embodiment of the method comprises:

(a) digesting the maternal plasma sample with a methylation-sensitive restriction enzyme which recognizes the methylation-sensitive restriction enzyme recognition site;

(b) contacting the digested sample with a stem-loop primer, wherein the 3' portion of the stem-loop primer is complementary to the 3' end of a strand of a digested fetal DNA fragment at the methylation-sensitive restriction enzyme recognition site, while the 5' portion of the stem-loop primer is capable of forming a stem-loop structure;

(c) annealing the stem-loop primer to the strand of the digested fetal DNA fragment via the 3' portion thereof and performing an extension reaction by using the strand of the restriction enzyme-digested DNA fragment as a template; and (d) detecting and/or quantifying the extension product with a PCR assay, wherein one primer of the primer pair used in the PCR assay is specific to the stem-loop primer, wherein results of the PCR assay indicate the presence and/or quantity of the hypomethylated fetal target DNA fragment in the maternal plasma sample.

According to a fifth aspect of the present invention, there is provided a kit for selectively amplifying a hypomethylated target DNA fragment in a sample containing a corresponding hypermethylated target DNA fragment, wherein both the hypomethylated target DNA fragment and the corresponding hypermethylated target DNA fragment contain a methylation-sensitive restriction enzyme recognition site. Due to the methylation-sensitive nature of the enzyme, the hypomethylated target will be cut but the hypermethylated target will not be cut. In an embodiment of the kit, it comprises:

(i) a methylation-sensitive restriction enzyme, which recognizes the methylation-sensitive restriction enzyme recognition site;

(ii) a stem-loop primer, wherein the 3' portion of the stem-loop primer is complementary to the 3' end of a strand of a digested target DNA fragment at the methylation-sensitive restriction enzyme recognition site, and the 5' portion of the stem-loop primer is capable of forming a stem-loop structure;

(iii) a DNA polymerase for extending the stem-loop primer by using the strand of the digested target DNA fragment as a template; and (iv) reagents for amplifying the stem-loop primer extension product.

These and other embodiments of the present invention are further described by the detailed description that follows.

BRIEF DESCRIPTION OF THE SEVERAL VIEWS OF THE DRAWINGS

FIG. 1 is a schematic diagram of an embodiment of the present invention for the detection of the placenta-derived hypomethylated SERPINB5 promoter in a maternal plasma sample, in which: (A) shows that the hypomethylated SERPINB5 molecule is digested by the HpaII enzyme, and HpaII digestion could not proceed if the target is hypermethylated; (B) shows that the stem-loop primer anneals to the 3' end of the enzyme digestion site; (C) shows the extension of the stem-loop primer and, as binding of the stem-loop primer to the undigested long DNA molecule is inefficient, no stem-loop extension product is expected to be generated from the hypermethylated DNA molecule; (D) shows that the quantity of the detectable enzyme-digested, stem-loop-extended SERPINB5 molecules is measured by a real-time PCR assay; and (E) shows that the placental specificity of the detectable enzyme-digested, stem-loop-extended SERPINB5 molecules in maternal plasma is verified by the genotyping assay on the SERPINB5-156 single-base variation.

FIG. 3 shows mass spectra illustrating stem-loop genotyping results on the SERPINB5-156 single-base variation, in which, in each spectrum, the x-axis depicts the molecular mass of the ions and the y-axis depicts the intensity in arbitrary units, wherein (A) shows a maternal plasma analysis of a pregnancy case with a combination of maternal AA and placental AC genotypes, and results from the enzyme-digested pre-delivery maternal plasma DNA showing that the correct placental-specific genotype was detected with the stem-loop primer protocol; and (B) shows a maternal plasma analysis of a pregnancy case with a combination of maternal AC and placental AA genotypes, and results showing that only the placenta-derived "A" peak was observed in the enzyme-digested, stem-loop primer extended pre-delivery maternal plasma DNA.

DETAILED DESCRIPTION

Definitions

Unless defined otherwise, all technical and scientific terms used herein have the meaning commonly understood by a person skilled in the art to which this invention pertains. As used herein, the following terms have the meanings as defined unless specified otherwise.

A "polynucleotide," as used herein, refers to a polymer of nucleotides of any length. A polynucleotide may comprise modified nucleotides, such as methylated nucleotides.

A "primer," as used herein, refers to a nucleotide sequence, generally with a free 3'-OH group, that hybridizes with a template sequence (such as a target polynucleotide or target DNA) and is capable of promoting polymerization of a polynucleotide complementary to the template. A "primer" can be, for example, an oligonucleotide. The term "oligonucleotide" generally refers to short, generally single stranded, generally synthetic polynucleotides that are usually, but not necessarily, less than about 200 nucleotides in length.

A "template," or "template strand," as used herein, is a polynucleotide for which amplification is desired. The template sequence may be known or not known, in terms of its actual sequence.

"Amplification," or "amplifying," as used herein, generally refers to the process of producing multiple copies of a desired sequence or its complement.

A "polymerase chain reaction" or "PCR" means a reaction for in vitro amplification of a specific DNA sequence by simultaneous primer extension of the complementary strands of the DNA. In other words, PCR is a reaction for making multiple copies or replicates of a target nucleic acid flanked by primer binding sites, such reaction comprising one or more repeats of the following steps: (i) denaturing the target nucleic acid, (ii) allowing primers to bind to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art. For example, in a conventional PCR using Taq DNA polymerase, a double-stranded target nucleic acid may be denatured at a temperature >90° C., primers bound at a temperature in the range of 50-75° C., and primers extended at a temperature in the range of 72-78° C. A "Real-time PCR" means a PCR for which the amount of a reaction product, i.e. amplicon, is monitored as the reaction proceeds. There are many forms of real-time PCR that differ mainly in the probes used for monitoring the reaction product. One type of the probe is a fluorescent indicator. Generally, the fluorescent indicator has an oligonucleotide specific to a target sequence, and a fluorescent molecule in proximity to a fluorescent quencher until the oligonucleotide moiety to which they are attached specifically binds to the amplification product.

A "portion", "part" or "region," used interchangeably herein, of a polynucleotide or oligonucleotide is a contiguous sequence of 2 or more bases. In some embodiments, a region, part or portion is at least about any of 3, 5, 10, 15, 20, 25 or more contiguous nucleotides.

The terms "3' portion" or "3' region", as used interchangeably herein, refers to the portion or region of a polynucleotide or oligonucleotide located at the 3' end of the polynucleotide or oligonucleotide. Similarly, the terms "5' portion" and "5' region", used interchangeably herein, refer to the portion or region of a polynucleotide or oligonucleotide located at the 5' end of the polynucleotide or oligonucleotide.

As used herein, the term "methylation-sensitive restriction enzyme recognition site" refers to a region of a DNA molecule, which can be recognized and then cleaved by a methylation-sensitive restriction enzyme when it is unmethylated.

As used herein, "hypomethylated DNA" or "hypomethylated DNA fragment" means a DNA or DNA fragment in which most of the CpG sites are not methylated. In particular, when they are used in combination with a methylation-sensitive restriction enzyme recognition site, it is intended to mean that the methylation-sensitive restriction enzyme recognition site is unmethylated and may be cleaved by a methylation-sensitive restriction enzyme. Similarly, "hypermethylated DNA" or "hypermethylated DNA fragment" means a DNA or DNA fragment in which most of the CpG sites are methylated. In particular, when they are used in combination with a methylation-sensitive restriction enzyme recognition site, it is intended to mean that the methylation-sensitive restriction enzyme recognition site is methylated and may not be cleaved by a methylation-sensitive restriction enzyme.

When a primer used in a PCR assay is "specific" to a DNA molecular, especially to a stem-loop primer of the present invention, it is intended to mean that at least a part of the primer is complementary to the DNA sequence or has the same nucleotide sequence as the DNA molecule.

As used herein, "a corresponding hypermethylated DNA fragment" of a hypomethylated DNA fragment is intended to mean that the hypermethylated DNA fragment is substantially identical to the hypomethylated DNA fragment in terms of nucleotide sequence when properly aligned, but it is hypermethylated. The term "substantially identical to" means there may be one or more single-base variations, such as those known as "single nucleotide polymorphism", between these two DNA fragments. In addition, the term "corresponding" used herein does not mean these two DNA fragment necessarily have the same size.

A "sample," as used herein, means a quantity of material from a biological, medical, or patient source in which detection or quantification of target DNA fragments is sought. Typically, a sample may be a blood or plasma specimen.

The terms "a" and "an", as used herein, do not denote a limitation of quantity, but rather denote the presence of at least one of the referenced items.

Stem-Loop Primers

Figure 1:
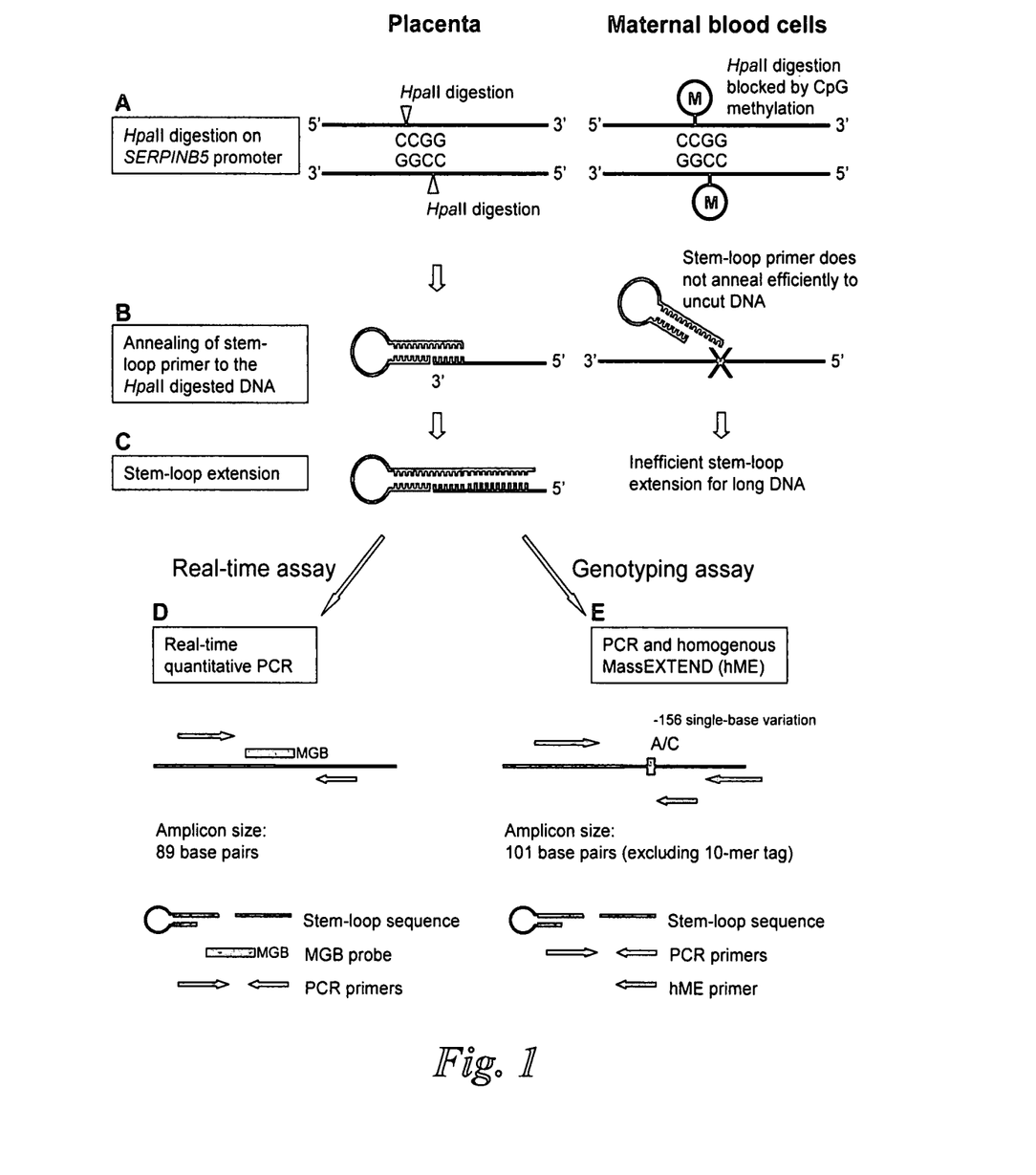

The stem-loop primer used in the present invention is generally a synthetic oligonucleotide, which consists of a 3' portion and a 5' portion. The 3' portion of the stem-loop primer is single-stranded and is designed to be hybridizable or complementary to the 3' region of an oligonucleotide, such as, but not restricted to, a restriction enzyme-digested DNA fragment for which amplification is desired. In certain clinical samples, e.g. plasma, serum and urine, in which the nucleic acids are already partially fragmented, this approach can also be applied without prior restriction enzyme digestion. In such situations, more than one stem-loop primer may need to be used, so as to cover a number of possible 3' end sequences of the nucleic acid molecules in the specimen. It is further possible that the 3' end of the stem-loop primer can be synthesized in a degenerate manner, so as to cover all possible 3' end sequences. Another possibility is that inosine can be incorporated into selected bases at the 3' end of the stem-loop primer so as to expand the range of sequences in which the stem-loop primer can amplify. The 5' portion of the stem-loop primer is capable of forming a stem-loop structure under normal assay conditions. The term "stem-loop structure" used herein is intended to mean the "stem" region is a double-stranded region formed by intramolecular base pairing, while the "loop" region is a single-stranded region, as shown in FIG. 1. Typically, the 3' portion of the stem-loop primer of the present invention ranges from 4 to 15 bases, preferably from six to eight bases. Typically, the 5' portion of the stem-loop primer of the present invention ranges from 26 to 54 bases, preferably from 36 to 44 bases, in which the stem region ranges from five to 14 base pairs.

Digestion with Methylation-Sensitive Restriction Enzymes

Certain embodiments of the present invention involve the use of a methylation-sensitive restriction enzyme to digest a target DNA fragment in a sample. The target DNA fragment is selected such that it contains at least one methylation-sensitive restriction enzyme recognition site which may or may not be methylated.

The methods of the present invention make use of a methylation-sensitive restriction enzyme which preferentially cleaves unmethylated sequences compared to methylated sequences. After the restriction digestion, the hypomethylated target DNA fragment is cleaved, while the hypermethylated target DNA fragment remains uncleaved in the sample. Therefore, the hypomethylated target DNA fragment is distinguished from the hypermethylated target DNA fragment by the methylation-sensitive restriction enzyme.

Examples of such methylation-sensitive restriction enzymes include, but not limited to, AatII, AciI, AclI, AfeI, AgeI, AscI, AsiSI, AvaI, BceAI, BmgBI, BsaAI, BsaHI, BsiEI, BsiWI, BsmBI, BspDI, BsrFI, BssHII, BstBI, BstUI, ClaI, EagI, FauI, FseI, FspI, HaeII, HgaI, HhaI, HinP1I, HpaII, Hpy99I, HpyCH4IV, KasI, MluI, NaeI, NarI, NgoMIV, NotI, NruI, PmlI, PvuI, RsrII, SacII, SalI, SfoI, SgrAI, SmaI and SnaBI.

Annealing and Extension Reactions

After a methylation-sensitive restriction enzyme digestion, the sample is heated to a suitable temperature to denature the restriction enzyme-digested target DNA fragment, and then cooled to allow the stem-loop primer to bind to the primer binding site, i.e., the 3' end of a strand of a digested target DNA fragment at the restriction enzyme site. The term "annealing", as used throughout the specification, is intended to include both the denaturation and binding steps. However, in the case that the sample was already denatured, the term "annealing" would only include the binding step. Due to the stem-loop structure of the 5' portion of the stem-loop primer, binding of the stem-loop primer to an undigested target DNA fragment is not efficient. That is, during the annealing process, the stem-loop primer of the present invention preferentially or selectively binds a restriction enzyme-digested target DNA fragment when compared to an undigested target DNA fragment.

The extension of the stem-loop primer is usually carried out with a DNA polymerase. The sequence of nucleotides added in the extension process is determined by the sequence of the template polynucleotide. As the stem-loop primer selectively binds a restriction enzyme-digested target DNA fragment as described above, the extension reaction will use the restriction enzyme-digested target DNA fragment as a template, and no extension product is expected to be generated from undigested target DNA fragments.

Typically, the enzyme-digested DNA fragment is denatured with the extension mixture, including the stem-loop primer, to maximize the chance of a stem-loop primer binding to a target DNA fragment. Although it is less preferable, it is applicable that the stem-loop primer is added to the sample after the sample is denatured, and then cooled to permit the binding. A polymerase is then added and the whole mixture is subjected to the stem-loop primer extension.

Detecting and/or Quantifying Stem-Loop Primer Extension Products

Generally, detecting and/or quantifying the stem-loop primer extension product are performed by using a PCR assay. In order to selectively amplify the stem-loop primer extension product, one primer of the primer pair used in the PCR assay is designed such that it is specific to the stem-loop primer. The other one of the primer pair used in the PCR assay is designed to be specific to the digested target DNA fragment. The amplification product will be a DNA fragment flanked by these two primers. Where the stem-loop primer extension product serves as a template for PCR, the extension of PCR primers will unfold the stem-loop structure.

In a preferred embodiment of the present invention, the PCR assay is a real-time PCR assay. The probe used in the real-time PCR assay is preferably specific to the 3' portion of the stem-loop primer to further increase the specificity of the detection or quantification.

Selectively Amplifying Target DNA Fragments with Specific End Sequences

In an aspect of the present invention, there is provided a method for selectively amplifying a target DNA fragment with a specific end sequence in a sample containing other DNA fragments, the method comprising:

(a) contacting the sample with a stem-loop primer, wherein the 3' portion of the stem-loop primer is complementary to the 3' end of a strand of the target DNA fragment on the specific end sequence, and the 5' portion of the stem-loop primer is capable of forming a stem-loop structure;

(b) annealing the stem-loop primer to the strand of the digested DNA fragment via the 3' portion thereof and performing an extension reaction by using the strand of the DNA fragment as a template; and (c) amplifying the extension product to obtain an amplified product of the target DNA fragment.

In an embodiment, the target DNA fragment with a specific end sequence is present in the sample (e.g. plasma, serum and urine) naturally. In another embodiment, the target DNA fragment is generated by enzyme digestion. Preferably, the enzyme is a restriction enzyme, especially a methylation-sensitive restriction enzyme.

In some embodiments, a plurality of stem-loop primers are used to selectively amplify a plurality of target DNA fragments. In these embodiments, each of the stem-loop primers is specific to each of the target DNA fragments respectively.

In an embodiment of the method, the step of amplifying the extension product is achieved by using a PCR amplification, in which one primer of the primer pair is specific to the stem-loop primer. To detect and/or quantify the extension product, a real-time PCR amplification is preferably used to amplify the extension product, in which one primer of the primer pair is specific to the stem-loop primer. If the probe used in the real-time PCR amplification is specific to the 3' portion of the stem-loop primer, the specificity of the detection and/or quantification can be further improved.

The use of a stem-loop primer of the present invention also provides improved specificity over traditional amplification methods. Due to the stem-loop structure of the 5' portion of the stem-loop primer, in the annealing process the stem-loop primer will not likely bind a DNA fragment at the internal region thereof having a sequence substantially identical to the 3' end of a target DNA fragment. Moreover, due to the base stacking, the thermal stability of the stem-loop primer/target DNA fragment complex is increased. Thus, the stem-loop primer is very useful for distinguishing a target DNA fragment from non-target DNA fragments.

In addition, the use of a stem-loop primer of the present invention extends the length of a target DNA fragment to be amplified. This will be useful in the case that the target is a short DNA fragment, e.g. not longer than 100 base pairs, especially not longer than 30 base pairs. The extension of a short DNA fragment provides bigger room for designing primers for a subsequent PCR amplification.

Selectively Amplifying Hypomethylated Target DNA Fragments

Conventionally, the use of methylation-sensitive restriction endonucleases involves the digestion of unmethylated CpG sites in a DNA sequence so as to selectively amplify the uncut DNA sequence containing methylated CpG sites by PCR amplification. In the case that the unmethylated DNA is the target, the use of bisulfite conversion seems to be an unavoidable step. Therefore, the positive detection of the cleaved hypomethylated molecules would be desired.

In an aspect of the present invention, there is provided a method for selectively amplifying a hypomethylated target DNA fragment which has been cut by a methylation-sensitive restriction enzyme in a sample containing a corresponding hypermethylated DNA fragment which is not cut by the enzyme. One embodiment of the method comprises:

(a) contacting the sample with a stem-loop primer, wherein the 3' portion of the stem-loop primer is complementary to the 3' end of a strand of the hypomethylated target DNA fragment at the cut site, and the 5' portion of the stem-loop primer is capable of forming a stem-loop structure;

(b) annealing the stem-loop primer to the strand of the hypomethylated target DNA fragment via the 3' portion thereof and performing an extension reaction by using the strand of the restriction enzyme-digested target DNA fragment as a template; and (c) amplifying the extension product to obtain an amplified product of the hypomethylated target DNA fragment.

In an embodiment of the method, the hypomethylated target DNA fragment and the corresponding hypermethylated target DNA fragment in a sample are derived from a gene of the same individual. In a preferred embodiment of the method, the hypomethylated target DNA fragment in a sample is derived from a gene of a fetus, for example, its placenta, and the corresponding hypermethylated target DNA fragment in the sample is derived from the same gene of the pregnant mother. In another embodiment of the method, the sample is a blood or plasma specimen in a desired volume.

In an embodiment of the method, the step of amplifying the extension product is achieved by using a PCR amplification, in which one primer of the primer pair is specific to the stem-loop primer. To detect and/or quantify the extension product, a real-time PCR amplification is preferably used to amplify the extension product, in which one primer of the primer pair is specific to the stem-loop primer. If the probe used in the real-time PCR amplification is specific to the 3' portion of the stem-loop primer, the specificity of the detection and/or quantification can be further improved.

The present invention also provides a kit for selectively amplifying a hypomethylated target DNA fragment in a sample containing a corresponding hypermethylated target DNA fragment, wherein both the hypomethylated target DNA fragment and the corresponding hypermethylated target DNA fragment contain a methylation-sensitive restriction enzyme recognition site. One embodiment of the kit comprises:

(i) a methylation-sensitive restriction enzyme, which recognizes the methylation-sensitive restriction enzyme recognition site;

(ii) a stem-loop primer, wherein the 3' portion of the stem-loop primer is complementary to the 3' end of a strand of a digested target DNA fragment at the methylation-sensitive restriction enzyme recognition site, and the 5' portion of the stem-loop primer is capable of forming a stem-loop structure;

(iii) a DNA polymerase for extending the stem-loop primer by using the strand of the digested target DNA fragment as a template; and (iv) reagents for amplifying the stem-loop primer extension product.

In an embodiment of the present invention, the reagents for amplifying the stem-loop primer extension product include those for PCR amplification, such as primers, a dNTP mixture and a Taq DNA polymerase, wherein one primer of the primer pair is specific to the stem-loop primer. Preferably, the PCR amplification is a real-time PCR amplification, and the reagents further include a probe for monitoring the process of the amplification. More preferably, the probe has a sequence specific to the 3' portion of the stem-loop primer.

The methods of the present invention are further explained by way of the following examples. In these samples, the SERPINB5 promoter is used as a hypomethylated target DNA fragment. However, it will be understood by one skilled in the art that the present invention is not limited to the SERPINB5 promoter. Other hypomethylated DNA molecules which may be mentioned herein include CGI #137 as disclosed in Yamada et al., *Genome Res* 14, 247-266 (2004) as well as in U.S. patent application Ser. No. 11/144,951 to Lo et al., titled "Marker for prenatal diagnosis and monitoring" and U.S. Provisional Patent Application No. 60/797,456, phosphodiesterase 9A (PDE9A), *Homo sapiens* protein phosphatase 1, regulatory (inhibitor) subunit 2 pseudogene 2 (PPP1R2P2), and Similarity to Fem1A (*Caenorhabditis elegans*). Therefore, the following examples are provided by way of illustration only and not by way of limitation.

Examples

Materials and Methods

Mechanism of Stem-Loop Primer Mediated Amplification

The mechanism of the stem-loop primer extension on fragmented DNA is illustrated in FIGS. 1A to 1C, taking the SERPINB5 promoter as an example of the target DNA. After restriction enzyme digestion, the SERPINB5 promoter would be cut at specific restriction sites. The stem-loop primer was designed in such a way that the last few nucleotides on the 3' portion were complementary to the 3' end of the enzyme restriction site on the SERPINB5 promoter (FIG. 1B). In our assay, the complementary number of bases on the 3' portion of the stem-loop primer to anneal to the SERPINB5 promoter was six bases long.

The SERPINB5 promoter is hypomethylated in the placenta and hypermethylated in maternal blood cells (Chim, et al., *Proc Natl Acad Sci USA*, 102:14753-8 (2005)). Enzyme digestion was performed by HpaII, a methylation-sensitive restriction endonuclease which recognized and cut the DNA sequence CCGG, and its action would be blocked by CpG methylation. After enzyme digestion, a specific cut site would be created on the hypomethylated placental SERPINB5 DNA molecule, which would allow the stem-loop primer to anneal. For the hypermethylated DNA molecules that remained intact after enzyme digestion, the efficiency for stem-loop primer extension would be low. In our assays, the stem-loop primer annealed to the minus strand of the enzyme-digested SERPINB5 promoter and proceeded with the extension reaction. This extension product served as a template for the subsequent PCR. The detection of the enzyme-digested, stem-loop primer extended hypomethylated fetal DNA molecules in third trimester pre-delivery maternal plasma was demonstrated by using real-time quantitative PCR (FIG. 1D) and the fetal origin of the detected molecules was further confirmed by genotyping the SERPINB5-156 single-base variation (Tong, et al., *Clin Chem,* 52:2194-202 (2006)) (FIG. 1E).

Study Participants

Women with singleton uncomplicated pregnancies who attended the Department of Obstetrics and Gynaecology, Prince of Wales Hospital, Hong Kong, were recruited from September 2006 to December 2006. Informed consent was given by all participants, and ethics approval was obtained from the Institutional Review Board. Placental tissue samples were collected from 3rd-trimester pregnancies after elective cesarean delivery. Twelve milliliters of maternal peripheral blood samples were collected into EDTA tubes from all women before a cesarean section. An additional 12 mL of blood was collected into EDTA tubes from each of these women after delivery to demonstrate the postpartum clearance of the fetal DNA sequences.

Processing of Blood and Tissue Samples

Maternal peripheral blood samples were centrifuged at 1,600 g for 10 min at 4° C., and the plasma portion was recentrifuged at 16,000 g for 10 min at 4° C. (Chiu et al., *Clin Chem,* 47:1607-13 (2001)). The blood cell portion was recentrifuged at 2,500 g, and any residual plasma was removed. DNA from the peripheral blood cells and that from maternal plasma was extracted with the blood and body fluid protocol of the QIAamp DNA Blood Mini Kit (Qiagen, Hilden, Germany). DNA samples from the placentas were extracted with the QIAamp DNA Mini Kit (Qiagen) according to the manufacturer's tissue protocol.

Methylation-Sensitive Restriction Endonuclease Digestion

In order to create a specific end for a stem-loop primer to anneal to and extend on the target DNA, HpaII (New England Biolabs, Ipswich, Mass.), a methylation-sensitive restriction endonuclease, was used to digest the hypomethylated DNA. Extracted DNA was digested with the HpaII enzyme at 37° C. for 16 hours in a 20 µL reaction mixture. For placental tissue and maternal blood cells, 10 U of HpaII enzyme was used to digest 100 ng and 50 ng of DNA for the real-time PCR and genotyping assays, respectively. For plasma samples, 10 U of the HpaII enzyme was used to digest the DNA from 1.6 mL plasma. A mock-digested aliquot, labeled as undigested, was included for each sample. For mock-digestion, an equal amount of DNA was subjected to the same digestion condition without the addition of enzyme.

Stem-Loop Primer Extension and Real-Time Assay on Maternal Plasma

For stem-loop primer extension, 5 µL of the digestion products were mixed with 10 nM stem-loop primer (Integrated DNA Technologies, Coralville, Iowa, Table 1A), 1×RT buffer (Applied Biosystems, Foster City, Calif.), 0.25 mM each of dNTPs (Promega, Madison, Wis.), and the volume was made up to 14 µL with water. This mixture was denatured at 95° C. for 5 min, snap cooled on ice, and 50 U of MultiScribe reverse transcriptase (Applied Biosystems), which worked on both RNA and DNA as templates, was added. This 15 µL reaction was incubated at 4° C. for 5 min, 16° C. for 30 min, 42° C. for 30 min, and 85° C. for 5 min. All samples, including no-template controls, were run in duplicate, and the mean quantity was calculated. Placental DNA and maternal blood cell DNA were included as positive and negative controls, respectively.

Real-time TaqMan® assay for the SERPINB5 promoter sequence was performed on the HpaII digested, stem-loop primer extended DNA. 1.33 µL of the extension product was used for the real-time assay. Each 20 µL real-time PCR included 1× TaqMan® Universal PCR Master Mix (Applied Biosystems), 40 nM TaqMan® probe (Applied Biosystems), 300 nM forward primer (Integrated DNA Technologies) and 140 nM reverse primer (Integrated DNA Technologies). The sequences of the probe and primers are listed in Table 1A. The thermal profile was 95° C. for 10 min, followed by 40 cycles of 95° C. for 15 s, and 64° C. for 1 min.

Genotyping of SERPINB5-156 Single-Base Variation

Specificity of the stem-loop primer assay in amplifying the enzyme-digested, hypomethylated placental DNA molecules was further illustrated by assessing the genotype of the amplified enzyme-digested SERPINB5 molecules in maternal plasma samples collected from informative fetomaternal pairs. Paired placenta and maternal blood cell samples were genotyped, using a previously described protocol (Tong, et al., *Clin Chem,* 52:2194-202 (2006)), for the SERPINB5-156 single-base variation, which was an A/C variation. Any pairs showing different placental and maternal genotypes were deemed informative. The maternal plasma samples from those informative cases were subjected to analysis by a stem-loop genotyping protocol as described below.

Stem-Loop Primer Extension and Genotyping Assay on Maternal Plasma

The stem-loop genotyping protocol, differed from the stem-loop real-time protocol, was aimed at specifically genotyping the enzyme-digested plasma SERPINB5 amplified through the stem-loop primer extension. In order to maximize the input amount of plasma DNA for genotyping, all reaction products from the enzyme digestion reaction were used for the stem-loop primer extension as a large volume reaction. In the 56 µL reaction mixture, 10 nM stem-loop primer (Integrated DNA Technologies, Table 1B), 1×RT buffer (Applied Biosystems), and 0.25 mM each of dNTPs (Promega) were mixed with the digestion product. The mixture was then denatured at 95° C. for 5 min and snap cooled on ice. 200 U of MultiScribe reverse transcriptase (Applied Biosystems) was then added to the denatured DNA mixture and incubated at 4° C. for 5 min, 16° C. for 30 min, 42° C. for 30 min, and 85° C. for 5 min.

In a 200 µL PCR, 1× HotStar Taq PCR buffer with 1.5 mM $MgCl_2$ (Qiagen), an additional 1 mM $MgCl_2$, 200 µM dNTP mix (Promega), 750 nM of the forward primer (Integrated DNA Technologies, Table 1B), 350 nM of the reverse primer (Integrated DNA Technologies, Table 1B), and 4 U of HotStar Taq Polymerase were added with 53.2 µL of the stem-loop primer extended DNA template. The thermal profile was 95° C. for 15 min, followed by 50 cycles of 95° C. for 20 s, 56° C. for 30 s, and 72° C. for 1 min, plus a final incubation at 72° C. for 3 min. 25 µL of the PCR products were taken out and subjected to shrimp alkaline phosphatase (SAP) treatment to remove unincorporated dNTPs as previously described (Tong, et al., *Clin Chem,* 52:2194-202 (2006)).

The single-base variation genotyping was then performed on the SAP-treated PCR products by a primer extension reaction, the MassARRAY™ Homogenous MassEXTEND™ (hME). In brief, 771 nM of extension primer (Integrated DNA Technologies, Table 1B), 1.15 U Thermosequenase (Sequenom), and 64 µM each of ddATP, ddCTP, ddTTP and dGTP (Sequenom) in an extension cocktail were added to 10 µL of the SAP-treated PCR products. The thermal profile was 94° C. for 2 min, followed by 95 cycles of 94° C. for 5 s, 52° C. for 5 seconds, and 72° C. for 5 seconds. The allele-specific extension reactions were designed to generate products of distinct masses for each single-base variation that could be readily resolvable by Matrix-Assisted Laser-Desorption and Ionization Time-of-Flight Mass Spectrometry (MALDI-TOF MS) analysis. Data acquisition from the SpectroCHIP was done using the MassARRAY Analyzer Compact Mass Spectrometer (Sequenom). Mass data were imported into the MassARRAY Typer (Sequenom) software for analysis.

Statistical Analysis

Statistical analyses were performed using the SigmaStat 3.0 software (SPSS).

TABLE 1

Primers and other sequences for the real-time stem-loop assay and the genotyping stem-loop assay on the SERPINB5 gene promoter A. Real-Time SERPINB5 Assay

| | Sequences (5' to 3') | SEQ ID NO. |
|---|---|---|
| Stem-loop primer | GTCGTATCCAGTGCAGGGTCCGAGGT ATTCGCACTGGATACGAC<u>GTCCTG</u>[a] | 1 |
| TaqMan probe | 6-FAM-CGCACTGGATACGACGTC (MGB)[b] | 4 |
| Forward primer | TTACATGCATACGTACAGACATGCG | 2 |
| Reverse primer | AGTGCAGGGTCCGAGGTAT | 3 |

B. Genotyping SERPINB5-156 Single-Base Variation Assay

| | Sequences (5' to 3') | SEQ ID No. | Molecular Masses (Da) |
|---|---|---|---|
| Stem-loop primer | GTCGTATCCAGTGCAGGGTCCGA GGTATTCGCACTGGATACGAC<u>GTC CTG</u>[a] | 1 | NR[c] |
| Forward primer | ACGTTGGATGGGCAGGAAGGGGC TGTGAGTTACATG[d] | 5 | NR |
| Reverse primer | ACGTTGGATGGGTCCGAGGTATTC GCACTGGATACGAC[d] | 6 | NR |
| Extension primer | AGACATGCGTACGGCAA | 7 | 5228.4 |
| Extension product 1 | AGACATGCGTACGGCAAT | 8 | 5516.6 |
| Extension product 2 | AGACATGCGTACGGCAAGC | 9 | 5830.8 |

[a] Underlined nucleotides indicate the six bases on the 3' end of the stem-loop primer which are complementary to the target sequences for primer annealing.
[b] 6-FAM = 6-carboxyfluorescein, MGB = minor-groove binding.
[c] NR = not relevant.
[d] Bold nucleotides indicate the 10-mer tags added to the 5' end of the primers in such a way that the masses of the primers would fall out of the analytic range of the mass spectrometry.

Results and Discussion

Stem-Loop Primer Extension and Real-Time PCR Assay on Maternal Plasma with and without HpaII Enzyme Digestion We expect that the methylation-sensitive restriction enzyme, HpaII, would cut the hypomethylated SERPINB5 DNA sequences from the placenta and hence extendable by the stem-loop primer and detectable by PCR. However, when no restriction enzyme was added to the placental DNA, no restriction termini would be available for the stem-loop primer to anneal and to proceed with the extension step. On the other hand, as the SERPINB5 promoter was hypermethylated in maternal blood cells, we would expect no fragmentation and no stem-loop primer extension from the digestion reaction either with or without restriction enzyme. As a result, no signal was expected to be detectable from the subsequent PCR step.

When the placental DNA was digested with the HpaII enzyme, the percentage recovery of detectable SERPINB5 promoter sequence was observed to be an average of 5.91%. The percentage recovery was the quantity of detectable SERPINB5 promoter sequences expressed as a percentage of the original amount of DNA input into the reaction. Without HpaII enzyme digestion, no detectable signal was observed for the placental DNA.

When subjected to HpaII digestion followed by stem-loop primer extension, DNA from the maternal blood cells had not been showing any detectable signals. However, one of the duplicated wells in one particular run of the stem-loop protocol gave a low level of detectable enzyme-digested, stem-loop primer extended SERPINB5 promoter sequences. It gave a percentage recovery of 0.56%.

Figure 2:
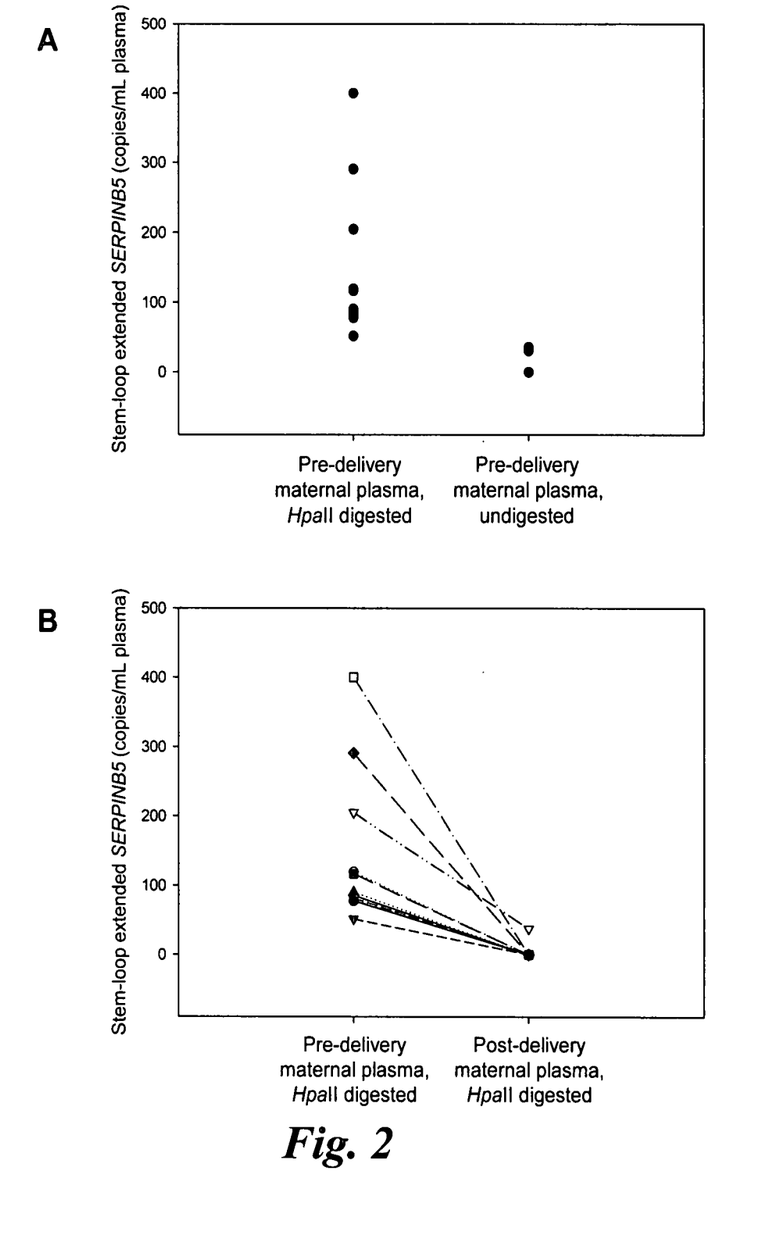
FIG. 2 (A) shows assay results of the hypomethylated SERPINB5 promoter in a maternal plasma sample with and without HpaII digestion, indicating that without enzyme addition, there were no/low levels of detectable signals from the same maternal plasma samples (P=0.001, Wilcoxon signed-rank test); and (B) shows assay results of the hypomethylated SERPINB5 promoter in pre-delivery and post-delivery maternal plasma samples, in which post-partum clearance was observed when comparing the enzyme-digested, stem-loop extended SERPINB5 promoter in pre-versus post-delivery maternal plasma (P=0.001, Wilcoxon signed-rank test).

Eleven pairs of pre- and post-delivery maternal plasma samples were subjected to the stem-loop real-time PCR assay. Comparison was made between HpaII-digested and undigested pre-delivery maternal plasma. Results showed that after HpaII enzyme digestion, the detectable SERPINB5 promoter sequence concentration in the pre-delivery maternal plasma ranged from 52-400 copies/mL plasma (Table 2). Without enzyme addition, the SERPINB5 promoter was not detectable in nine of the eleven cases. The two cases with detectable SERPINB5 promoter showed a concentration of less than 40 copies/mL plasma (Table 2). A statistically significant difference in the stem-loop primer extended SERPINB5 promoter concentrations was observed between HpaII-digested and undigested pre-delivery maternal plasma (P=0.001, Wilcoxon signed-rank test), as shown in FIG. 2A.

After confirming the effect of enzyme digestion on creating an extendable end on the placental SERPINB5 promoter in the maternal plasma, we proceeded to compare the enzyme-digested pre- and post-delivery maternal plasma. As described above, the stem-loop primer extended SERPINB5 promoter was detectable in all eleven pre-delivery maternal plasma after HpaII enzyme digestion (Table 2). For their paired post-delivery maternal plasma after enzyme digestion, post-partum clearance was observed (P=0.001, Wilcoxon signed-rank test), as shown in FIG. 2B.

TABLE 2

Real-Time Quantitative PCR Detection of HpaII-Digested, Stem-Loop Primer Extended SERPINB5 Promoter in Maternal Plasma

| | Copies/mL Plasma | | | |
|---|---|---|---|---|
| | Undigested | | HpaII digested | |
| Case | Pre-Delivery | Post-Delivery | Pre-Delivery | Post-Delivery |
| M2275 | 0 | 0 | 78[a] | 0 |
| M2469 | 30 | 0 | 119 | 0 |
| M2492 | 0 | 0 | 52 | 0 |
| M2494 | 0 | 0 | 205 | 38 |
| M2505 | 0 | 0 | 117 | 0 |
| M2509 | 0 | 0 | 400 | 0 |
| M2521 | 0 | 58 | 290 | 0 |
| M2526 | 0 | 0 | 86 | 0 |
| M2535 | 0 | 0 | 90 | 0 |
| M2551 | 36 | 125 | 82 | 0 |
| M2570 | 0 | 0 | 78 | 0 |

[a] Bold numbers indicate the measured quantities of the samples which are expected to have detectable enzyme-digested, stem-loop primer extended SERPINB5 molecules.

Genotyping of SERPINB5-156 Single-Base Variation

Among the thirty-two pairs of placentas and maternal blood cells genotyped for the SERPINB5-156 single-base variation, different placenta and maternal genotypes were observed in nine of them. Three pairs had a placental genotype of heterozygous AC and a maternal genotype of homozygous M. The remaining six pairs had an opposite fetomaternal genotype combination. Maternal plasma samples from these nine individuals were chosen for the genotyping of the placenta-derived, enzyme-digested hypomethylated SERPINB5 in maternal plasma.

Stem-Loop Primer Extension and Genotyping Assay on Maternal Plasma

DNA samples from the placenta and maternal blood cells of known genotypes (heterozygous AC) were used as controls. Results showed that after enzyme digestion, correct genotypes were consistently identified in the placental DNA. In the case of maternal blood cell DNA, non-specific signals were occasionally detected.

Figure 3:
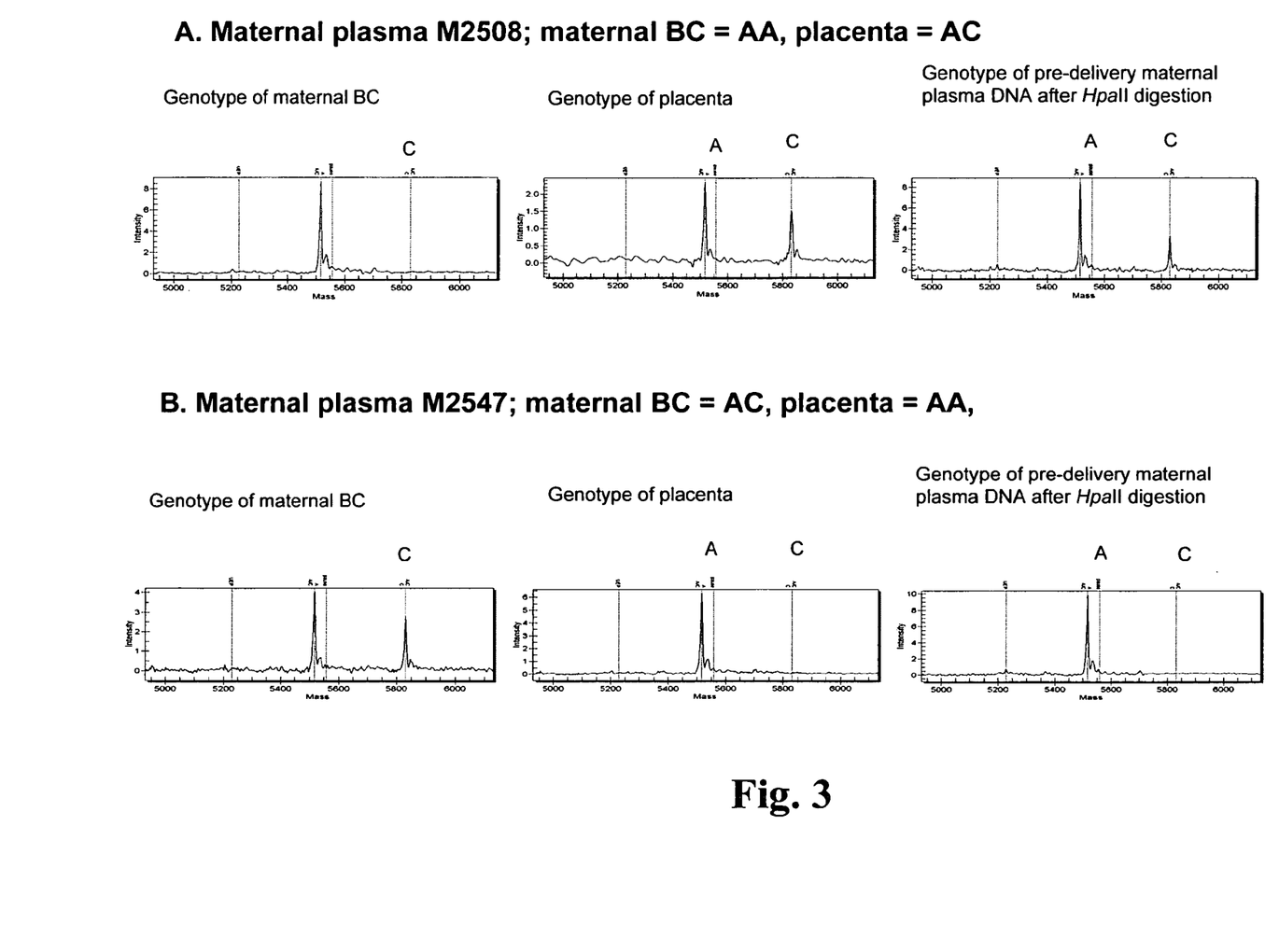

For our maternal plasma analysis, corresponding placental genotypes were correctly identified in all nine HpaII-digested, stem-loop primer extended pre-delivery maternal plasma DNA (Table 3). Representative mass spectra were shown in FIG. 3.

TABLE 3

Genotyping Results for HpaII-Digested, Stem-Loop Primer Extended SERPINB5 Promoter in Maternal Plasma

| | Genotype | | |
|---|---|---|---|
| Cases | Placenta | Maternal Blood Cells | HpaII-Digested Maternal Plasma |
| M2484 | AC | AA | AC |
| M2552 | AC | AA | AC |
| M2508 | AC | AA | AC |
| M2297 | AA | AC | AA |
| M2522 | AA | AC | AA |
| M2547 | AA | AC | AA |
| M2548 | AA | AC | AA |
| M2549 | AA | AC | AA |
| M2550 | AA | AC | AA |

In this study, we evaluated a new technique for amplifying and detecting DNA fragments which end in a particular sequence. This technique offers new possibility over conventional PCR-based approaches. For example, in previous approaches, even if a particular DNA fragment does not end in a particular sequence, as long as the PCR primer-binding sequence is within the fragment, then a particular PCR primer can bind. In the current approach, a stem-loop primer can only bind if the target sequence is situated at the end of the fragment. In one embodiment, such fragment ends are created by restriction enzymes. Using the SERPINB5 promoter as a model, the hypomethylated placental SERPINB5 molecules were successfully amplified and detected after methylation-sensitive restriction enzyme digestion. This stem-loop technique represents a useful technological advance for methylation studies since the protocol does not involve the use of bisulfite treatment, and it allows a selective amplification of the fragmented DNA molecules produced by restriction digestion.

Our quantitative real-time PCR results demonstrated that the hypomethylated placental SERPINB5 molecules were detectable by adding a stem-loop primer extension step after methylation-sensitive restriction enzyme digestion. On the other hand, detection of the hypermethylated maternal SERPINB5 molecules was of a low efficiency. The low level of signal detected from maternal DNA might be due to HpaII digestion on the rare maternal DNA molecules that were unmethylated at the site of enzyme cleavage. Previous results showed that the SERPINB5 promoter was close to, but not 100% methylated in maternal blood cells (Chim, et al., *Proc Natl Acad Sci USA*, 102:14753-8 (2005)). If these discrete cleavage events in maternal DNA were caught by the stem-loop primer, stem-loop primer extension and PCR amplification would continue. Since the stem-loop assay had a lowest detection limit of 6.25 copies/extension reaction, it was not surprising that an extremely low level of detectable HpaII digested SERPINB5 molecules was sporadically detected in maternal DNA.

The maternal plasma analysis showed that after HpaII enzyme digestion, stem-loop primer extension products were successfully detected in pre-delivery maternal plasma, which contained the hypomethylated placental SERPINB5. The "unexpected" detection of low levels of signals in pre-delivery maternal plasma without HpaII digestion and post-delivery maternal plasma with and without enzyme digestion could be explained by the fact that plasma DNA molecules are mainly short fragments, and the fetal derived ones are even shorter than the maternal ones, with 80% being shorter than 193 base pairs (Chan, et al., *Clin Chem*, 50:88-92 (2004)). Hence, there remains a chance where an occasional short maternal plasma DNA fragment terminates at the same nucleotide position as that would be created by HpaII digestion and become extendable. Nonetheless, the level of detectable SERPINB5 molecules showed a statistically significant difference between the HpaII-digested and undigested pre-delivery maternal plasma. In addition, post-partum clearance of these enzyme-digested, stem-loop primer extended SERPINB5 molecules was observed.

Further confirmation of the placental-origin of the HapII-digested, stem-loop primer extended SERPINB5 molecules in maternal plasma was demonstrated by the genotyping assay. Correct placental genotypes were consistently detectable in the placental DNA samples using the stem-loop genotyping protocol. Occasionally, primer extension products from the hME reaction were detectable from maternal blood cells. This observation could be explained by the same reason as for the real-time results that the SERPINB5 promoter is close to, but not 100% methylated. In addition, we used a large volume reaction for the genotyping experiments. Consequently, the "non-specific" signals could be due to the high sensitivity of the MassARRAY platform (Ding and Cantor, *Proc Natl Acad Sci USA*, 100:3059-64 (2003)). Results from the maternal plasma analysis revealed that when being subjected to the stem-loop protocol, the hypomethylated placental DNA molecules in the maternal plasma were preferentially amplified. The corresponding placental genotypes were detected in all nine pre-delivery maternal plasma samples having different maternal and placental genotypes.

In this study, we were able to demonstrate that the idea of using a stem-loop primer in extending and amplifying methylation-sensitive restriction enzyme-digested DNA was feasible. Since the fetal DNA molecules in maternal plasma are intrinsically short, the introduction of a stem-loop primer extension step may facilitate more flexibility in PCR assay design, given that as few as 21 nucleotides of the target sequence is required. We envision that when more of these hypomethylated placental molecules are discovered, this stem-loop technique would represent an alternative in circulating fetal epigenetic marker detection to bisulfite conversion. The application of this technique can also extend to the use of nonmethylation-sensitive restriction enzymes for the detection of cut DNA fragments for general molecular analyses.

Such a method would also have application to many diagnostic scenarios in which clinically relevant DNA fragments have a different size from the background nonclinically relevant DNA. Examples include: fetal DNA in maternal plasma in which the circulating fetal DNA is shorter than the background longer maternal DNA (Chan K C A et al., *Clin Chem*, 50: 88-92 (2004)); and mutant DNA in the plasma of cancer patients is enriched in the DNA of smaller molecular sizes (Diehl F et al., *Proc Natl Acad Sci USA,* 102: 16368-73 (2005)).

It should be understood that while the invention has been described in conjunction with the detailed description thereof, the foregoing description is intended to illustrate and not limit the scope of the invention.

The invention claimed is:

1. A method for selectively amplifying a hypomethylated target DNA fragment which has been cut by a methylation-sensitive restriction enzyme in a sample containing a corresponding hypermethylated DNA fragment which is not cut by the enzyme, the method comprising:
   (a) contacting the sample with a stem-loop primer, wherein the 3' portion of the stem-loop primer is complementary to the 3' end of a strand of the hypomethylated target DNA fragment at the cut site, and the 5' portion of the stem-loop primer is capable of forming a stem-loop structure;
   (b) annealing the stem-loop primer to the strand of the hypomethylated DNA fragment via the 3' portion thereof and performing an extension reaction by using the strand of the hypomethylated DNA fragment as a template; and
   (c) amplifying the extension product to obtain an amplified product of the hypomethylated target DNA fragment,
   wherein the hypomethylated target DNA fragment is at least a part of CGI37, phosphodiesterase 9A (PDE9A), *Homo sapiens* protein phosphatase 1, regulatory (inhibitor) subunit 2 pseudogene 2 (PPP1R2P2), or Similarity to Fem1A (*Caenorhabditis elegans*).

2. The method according to claim 1, wherein the 3' portion of the stem-loop primer ranges from 4 to 15 bases.

3. The method according to claim 2, wherein the 3' portion of the stem-loop primer ranges from 6 to 8 bases.

4. The method according to claim 1, wherein the size of the 5' portion of the stem-loop primer ranges from 26 to 54 bases.

5. The method according to claim 4, wherein the size of the 5' portion of the stem-loop primer ranges from 36 to 44 bases.

6. The method according to claim 1, wherein the step of amplifying the extension product in (c) is carried out by a PCR.

7. The method according to claim 6, wherein one primer of a primer pair used in the PCR is specific to the stem-loop primer.

8. The method according to claim 1, wherein the step of amplifying the extension product in (c) is carried out by a real-time PCR.

9. The method according to claim 8, wherein one primer of a primer pair used in the real-time PCR is specific to the stem-loop primer.

10. The method according to claim 8, wherein a probe used in the real-time PCR has a sequence specific to 3' portion of the stem-loop primer.

11. The method according to claim 1, wherein the methylation-sensitive restriction enzyme is selected from the group consisting of: AatII, AciI, AclI, AfeI, AgeI, AscI, AsiSI, AvaI, BceAI, BmgBI, BsaAI, BsaHI, BsiEI, BsiWI, BsmBI, BspDI, BsrFI, BssHII, BstBI, BstUI, ClaI, EagI, FauI, FseI, FspI, HaeII, HgaI, HhaI, HinP1I, HpaII, Hpy99I, HpyCH4IV, KasI, MluI, NaeI, NarI, NgoMIV, NotI, NnuI, PmlI, PvuI, RsnII, SacII, SalI, SfoI, SgrAI, SmaI and SnaBI.

12. The method according to claim 1, wherein the hypomethylated target DNA fragment is no longer than 100 base pairs.

13. The method according to claim 12, wherein the hypomethylated target DNA fragment is no longer than 30 base pairs.

14. A method for detecting and/or quantifying a hypomethylated target DNA fragment in a sample containing a corresponding hypermethylated target DNA fragment, wherein both the hypomethylated target DNA fragment and the corresponding hypermethylated target DNA fragment contain a methylation-sensitive restriction enzyme recognition site, the method comprising:
  (a) digesting the sample with a methylation-sensitive restriction enzyme which recognizes the methylation-sensitive restriction enzyme recognition site;
  (b) contacting the digested sample with a stem-loop primer, wherein the 3' portion of the stem-loop primer is complementary to the 3' end of a strand of a digested DNA fragment at the methylation-sensitive restriction enzyme recognition site, and the 5' portion of the stem-loop primer is capable of forming a stem-loop structure;
  (c) annealing the stem-loop primer to the strand of the restriction enzyme-digested DNA fragment via the 3' portion thereof and performing an extension reaction by using the strand of the digested DNA fragment as a template; and
  (d) detecting and/or quantifying the extension product with a PCR assay, wherein one primer of a primer pair used in the PCR assay is specific to the stem-loop primer,
  wherein results of the PCR assay indicate the presence and/or quantity of the hypomethylated target DNA fragment in the sample, and
  wherein the hypomethylated target DNA fragment is at least a part of CGI137, phosphodiesterase 9A (PDE9A), *Homo sapiens* protein phosphatase 1, regulatory (inhibitor) subunit 2 pseudogene 2 (PPP1R2P2), or Similarity to Fem1A (*Caenorhabditis elegans*).

15. The method according to claim 14, wherein 3' portion of the stem-loop primer ranges from 4 to 15 bases.

16. The method according to claim 15, wherein 3' portion of the stem-loop primer ranges from 6 to 8 bases.

17. The method according to claim 14, wherein the 5' portion of the stem-loop primer ranges from 26 to 54 bases.

18. The method according to claim 17, wherein the 5' portion of the stem-loop primer ranges from 36 to 44 bases.

19. The method according to claim 14, wherein the PCR assay is a real-time PCR assay.

20. The method according to claim 19, wherein a probe used in the real-time PCR assay has a sequence specific to 3' portion of the stem-loop primer.

21. The method according to claim 14, wherein the methylation-sensitive restriction enzyme is selected from the group consisting of: AatII, AciI, AclI, AfeI, AgeI, AscI, AsiSI, AvaI, BceAI, BmgBI, BsaAI, BsaHI, BsiEI, BsiWI, BsmBI, BspDI, BsrFI, BssHII, BstBI, BstUI, ClaI, EagI, FauI, FseI, FspI, HaeII, HgaI, HhaI, HinP1I, HpaII, Hpy99I, HpyCH4IV, KasI, MluI, NaeI, NarI, NgoMIV, NotI, NruI, PmlI, PvuI, RsnII, SacII, SalI, SfoI, SgrAI, SmaI and SnaBI.

22. The method according to claim 14, wherein the digested target DNA fragment is no longer than 100 base pairs.

23. The method according to claim 22, wherein the digested target DNA fragment is no longer than 30 base pairs.

24. A method for detecting and/or quantifying a hypomethylated fetal DNA fragment in a maternal plasma sample containing a corresponding hypermethylated maternal DNA fragment, wherein both the hypomethylated fetal DNA fragment and the corresponding hypermethylated maternal DNA fragment contain a methylation-sensitive restriction enzyme recognition site, the method comprising:
  (a) digesting the maternal plasma sample with a methylation-sensitive restriction enzyme which recognizes the methylation-sensitive restriction enzyme recognition site;
  (b) contacting the digested sample with a stem-loop primer, wherein the 3' portion of the stem-loop primer is complementary to the 3' end of a strand of a digested DNA fragment at the methylation-sensitive restriction enzyme recognition site, and the 5' portion of the stem-loop primer is capable of forming a stem-loop structure;
  (c) annealing the stem-loop primer to the strand of the digested DNA fragment via the 3' portion thereof and performing an extension reaction by using the strand of the digested DNA fragment as a template; and
  (d) detecting and/or quantifying the extension product with a PCR assay, wherein one primer of a primer pair used in the PCR assay is specific to the stem-loop primer,
  wherein results of the PCR assay indicate the presence and/or quantity of the fetal hypomethylated target DNA fragment in the maternal plasma sample, and
  wherein the fetal DNA target DNA fragment is at least a part of the gene CGI137, phosphodiesterase 9A (PDE9A), *Homo sapiens* protein phosphatase 1, regulatory (inhibitor) subunit 2 pseudogene 2 (PPP1R2P2), or Similarity to Fem1A (*Caenorhabditis elegans*).

25. The method according to claim 24, wherein the 3' portion of the stem-loop primer ranges from 4 to 15 bases.

26. The method according to claim 25, wherein the 3' portion of the stem-loop primer ranges from 6 to 8 bases.

27. The method according to claim 24, wherein the 5' portion of the stem-loop primer ranges from 26 to 54 bases.

28. The method according to claim 27, wherein the 5' portion of the stem-loop primer ranges from 36 to 44 bases.

29. The method according to claim 24, wherein the PCR assay is a real-time PCR assay.

30. The method according to claim 29, wherein a probe used in the real-time PCR assay has a sequence specific to 3' portion of the stem-loop primer.

31. The method according to claim 24, wherein the methylation-sensitive restriction enzyme is selected from the group consisting of: AatII, AciI, AclI, AfeI, AgeI, AscI, AsiSI, AvaI, BceAI, BmgBI, BsaAI, BsaHI, BsiEI, BsiWI, BsmBI, BspDI, BsnFI, BssHII, BstBI, BstUI, ClaI, EagI, FauI, FseI, FspI, HaeII, HgaI, HhaI, HinP1I, HpaII, Hpy99I, HpyCH4IV, KasI, MluI, NaeI, NarI, NgoMIV, NotI, NruI, PmlI, PvuI, RsnII, SacII, SalI, SfoI, SgrAI, SmaI and SnaBI.

32. The method according to claim 24, wherein the digested DNA fragment is no longer than 100 base pairs.

33. The method according to claim 32, wherein the digested DNA fragment is no longer than 30 base pairs.

34. A kit for selectively amplifying a hypomethylated target DNA fragment in a sample containing a corresponding hypermethylated target DNA fragment, wherein both the hypomethylated target DNA fragment and the corresponding hypermethylated target DNA fragment contain a methylation-sensitive restriction enzyme recognition site, the kit comprising:
  (i) a methylation-sensitive restriction enzyme, which recognizes the methylation-sensitive restriction enzyme recognition site;
  (ii) a stem-loop primer, wherein the 3' portion of the stem-loop primer is complementary to the 3' end of a strand of a digested target DNA fragment at the methylation-sensitive restriction enzyme recognition site, and the 5' portion of the stem-loop primer is capable of forming a stem-loop structure;
  (iii) a DNA polymerase for extending the stem-loop primer by using the strand of the digested target DNA fragment as a template; and
  (iv) reagents for amplifying the stem-loop primer extension product,
  wherein the hypomethylated target DNA fragment is at least a part of the gene CGI137, phosphodiesterase 9A (PDE9A), *Homo sapiens* protein phosphatase 1, regulatory (inhibitor) subunit 2 pseudogene 2 (PPP1R2P2), or Similarity to Fem1A (*Caenorhabditis elegans*).

35. The kit according to claim 34, wherein the 3' portion of the stem-loop primer ranges from 4 to 15 bases.

36. The kit according to claim 35, wherein the 3' portion of the stem-loop primer ranges from 6 to 8 bases.

37. The kit according to claim 34, wherein the 5' portion of the stem-loop primer ranges from 26 to 54 bases.

38. The kit according to claim 37, wherein the 5' portion of the stem-loop primer ranges from 36 to 44 bases.

39. The kit according to claim 34, wherein the reagents for amplifying the stem-loop primer extension product are selected from those suitable for PCR amplification.

40. The kit according to claim 39, wherein the reagents for amplifying the stem-loop primer extension product comprise a primer pair for the PCR amplification, and wherein one primer of the primer pair is specific to the stem-loop primer.

41. The kit according to claim 34, wherein the reagents for amplifying the stem-loop primer extension product are selected from those suitable for real-time PCR.

42. The kit according to claim 41, comprising a probe that has a sequence specific to the 3' portion of the stem-loop primer.

43. The kit according to claim 34, wherein the methylation-sensitive restriction enzyme is selected from the group consisting of: AatII, AciI, AclI, AfeI, AgeI, AscI, AsiSI, AvaI, BceAI, BmgBI, BsaAI, BsaHI, BsiEI, BsiWI, BsmBI, BspDI, BsnFI, BssHII, BstBI, BstUI, ClaI, EagI, FauI, FseI, FspI, HaeII, HgaI, HhaI, HinP1I, HpaII, Hpy99I, HpyCH4IV, KasI, MluI, NaeI, NarI, NgoMIV, NotI, NruI, PmlI, PvuI, RsnII, SacII, SalI, SfoI, SgrAI, SmaI and SnaBI.

* * * * *

UNITED STATES PATENT AND TRADEMARK OFFICE
CERTIFICATE OF CORRECTION

Page 1 of 2

PATENT NO.         : 8,748,100 B2
APPLICATION NO.    : 11/897654
DATED              : June 10, 2014
INVENTOR(S)        : Yuk Ming Dennis Lo et al.

It is certified that error appears in the above-identified patent and that said Letters Patent is hereby corrected as shown below:

On the title page

Item (56):
"Chim, Stephen S.C. et al., "Detection of the Placental Epigenetic Signature of the *Maspin*Gene in Maternal Plasma," *PNAS41*(102): 14753-14758, October 11, 2005," should read, --Chim, Stephen S.C. et al., "Detection of the Placental Epigenetic Signature of the *Maspin Gene* in Maternal Plasma," *PNAS 41*(102): 14753-14758, October 11, 2005.--.

Item (56):
"Tong, Yu K. et al., "Noninvasive Prenatal Detection of Fetal Trisomy 18 by Epigenetic Allelic Ratio Analysis in Maternal Plasma: Theoretical and Empirical Considerations," *Clinical Chemistry*52(12): 2194-2202, 2006." should read, --Tong, Yu K. et al., "Noninvasive Prenatal Detection of Fetal Trisomy 18 by Epigenetic Allelic Ratio Analysis in Maternal Plasma: Theoretical and Empirical Considerations," *Clinical Chemistry 52* (12): 2194-2202, 2006.--.

In the claims

Column 20, line 57:
"RsnII, SacII, SaII, SfoI, SrgAI, SmaI and SnaBI," should read, --RsrII, SacII, SaII, SfoI, SrgAI, SmaI, and SnaBI--.

Column 21, line 48:
"RsnII, SacII, SaII, SfoI, SrgAI, SmaI and SnaBI," should read, --RsrII, SacII, SaII, SfoI, SrgAI, SmaI and SnaBI--.

Column 22, line 39:
"RsnII, SacII, SaII, SfoI, SrgAI, SmaI and SnaBI," should read, --RsrII, SacII, SaII, SfoI, SrgAI, SmaI and SnaBI--.

Signed and Sealed this
Twelfth Day of April, 2016

Michelle K. Lee
*Director of the United States Patent and Trademark Office*

CERTIFICATE OF CORRECTION (continued)
U.S. Pat. No. 8,748,100 B2

In the claims

Column 23, line 31:
"RsnII, SacII, SaII, SfoI, SrgAI, SmaI and SnaBI," should read, --RsrII, SacII, SaII, SfoI, SrgAI, SmaI and SnaBI--.

SEQUENCE LISTING

```
<160> NUMBER OF SEQ ID NOS: 9

<210> SEQ ID NO 1
<211> LENGTH: 50
<212> TYPE: DNA
<213> ORGANISM: Artificial Sequence
<220> FEATURE:
<223> OTHER INFORMATION: Stem-loop primer

<400> SEQUENCE: 1
gtcgtatcca gtgcagggtc cgaggtattc gcactggata cgacgtcctg          50

<210> SEQ ID NO 2
<211> LENGTH: 25
<212> TYPE: DNA
<213> ORGANISM: Artificial Sequence
<220> FEATURE:
<223> OTHER INFORMATION: Forward primer

<400> SEQUENCE: 2
ttacatgcat acgtacagac atgcg                                     25

<210> SEQ ID NO 3
<211> LENGTH: 19
<212> TYPE: DNA
<213> ORGANISM: Artificial Sequence
<220> FEATURE:
<223> OTHER INFORMATION: Reverse  primer

<400> SEQUENCE: 3
agtgcagggt ccgaggtat                                            19

<210> SEQ ID NO 4
<211> LENGTH: 18
<212> TYPE: DNA
<213> ORGANISM: Artificial Sequence
<220> FEATURE:
<223> OTHER INFORMATION: Probe

<400> SEQUENCE: 4
cgcactggat acgacgtc                                             18

<210> SEQ ID NO 5
<211> LENGTH: 36
<212> TYPE: DNA
<213> ORGANISM: Artificial Sequence
<220> FEATURE:
<223> OTHER INFORMATION: Forward primer

<400> SEQUENCE: 5
acgttggatg ggcaggaagg ggctgtgagt tacatg                         36

<210> SEQ ID NO 6
<211> LENGTH: 38
<212> TYPE: DNA
<213> ORGANISM: Artificial Sequence
<220> FEATURE:
<223> OTHER INFORMATION: Reverse primer

<400> SEQUENCE: 6
```

-continued

```
acgttggatg ggtccgaggt attcgcactg gatacgac                           38

<210> SEQ ID NO 7
<211> LENGTH: 17
<212> TYPE: DNA
<213> ORGANISM: Artificial Sequence
<220> FEATURE:
<223> OTHER INFORMATION: Extension primer

<400> SEQUENCE: 7
agacatgcgt acggcaa                                                  17

<210> SEQ ID NO 8
<211> LENGTH: 18
<212> TYPE: DNA
<213> ORGANISM: Artificial Sequence
<220> FEATURE:
<223> OTHER INFORMATION: Extension product

<400> SEQUENCE: 8
agacatgcgt acggcaat                                                 18

<210> SEQ ID NO 9
<211> LENGTH: 19
<212> TYPE: DNA
<213> ORGANISM: Artificial Sequence
<220> FEATURE:
<223> OTHER INFORMATION: Extension product

<400> SEQUENCE: 9
agacatgcgt acggcaagc                                                19
```